United States Patent [19]

Bucalo

[11] 3,991,743

[45] Nov. 16, 1976

[54] CONCEPTION-PREVENTING AND VARIABLE FILTERING OR FLOW CONTROL DEVICES AND METHODS

[76] Inventor: Louis Bucalo, 155 Roberts St., Holbrook, N.Y. 11741

[22] Filed: Oct. 9, 1974

[21] Appl. No.: 513,292

[52] U.S. Cl. .................. 128/1 R; 128/DIG. 25; 210/223; 138/43; 138/46; 251/65; 251/139
[51] Int. Cl.² ........................................ A61B 19/00
[58] Field of Search ............ 128/1 R, 130, DIG. 25, 128/303; 251/65, 129, 139; 210/222, 223; 138/43, 46; 137/251, 599, 807

[56] References Cited
UNITED STATES PATENTS

| | | | |
|---|---|---|---|
| 2,939,673 | 6/1960 | Rosholt | 251/139 |
| 2,943,739 | 7/1960 | Maynard | 210/223 |
| 3,422,813 | 1/1969 | Braley et al. | 128/1 R |
| 3,477,948 | 11/1969 | Inoue | 210/223 X |
| 3,556,156 | 1/1971 | Fuller | 138/43 |
| 3,627,678 | 12/1971 | Marston et al. | 210/222 |
| 3,731,670 | 5/1973 | Loe | 128/1 R |
| 3,742,933 | 7/1973 | Bucalo | 128/1 R |
| 3,868,973 | 3/1975 | Bierman et al. | 138/43 |

*Primary Examiner*—Dalton L. Truluck
*Attorney, Agent, or Firm*—Steinberg and Blake

[57] ABSTRACT

Devices and methods for preventing conception as well as for general use in variable filtering. For preventing conception at least temporarily the devices and methods provide a selective flow for fluid in a vas deferens with sperm being acted upon at the flow path in a manner which will prevent fluid which flows beyond the selective flow path from carrying viable sperm in numbers sufficient for conception. By regulating the size of the selective flow it is possible to achieve a variable filtering or flow controlling action which is of general utility.

38 Claims, 17 Drawing Figures

CONCEPTION-PREVENTING AND VARIABLE FILTERING OR FLOW CONTROL DEVICES AND METHODS

BACKGROUND OF THE INVENTION

The present invention relates to conception preventing devices and methods as well as to methods and devices which are of general utility in connection with variable filtering and flow control.

As it is well known, it is possible to prevent conception by interrupting the flow of fluid through the vas deferentia of a male. For example, by way of conventional vasectomies, a part of a vas deferens is removed and the ends of the vas deferens adjacent the removed part thereof are closed. Such vasectomies have the disadvantage of being irreversible for all practical purposes, and therefore it has been proposed to introduce into a vas deferens various types of devices such as valves and the like for enabling a reversible interruption of fluid flow through the vas deferens to be achieved.

However, it has been found that all of the above types of procedures and devices have a serious disadvantage in that highly undesirable results accompany the total interruption in fluid flow through the vas deferens for any substantial period of time. Experience has shown that the fluid which flows through the vas deferens serves not to carry sperm but also to perform other functions such as supplying certain hormones and enzymes to the body, maintaining the lumen of the vas deferens in a open condition enabling fluid to flow properly therethrough, and avoiding undesirable buildup of pressure. Thus, even where a device such as a valve is utilized for reversing the conception-preventing condition, there is an undesirable blockage of flow through the vas deferens. The result is that certain hormones and enzymes fail to be supplied because of the total blockage of fluid flow through the vas deferens. In addition, since there is a total interruption in fluid flow downstream of such a valve or other interruption in the lumen of the vas deferens, there is a tendency for the vas deferens to close upon itself downstream of the location where fluid-flow is blocked. Under these conditions when reversal is desired, as by opening of a previously implanted valve, fluid flow cannot be reliably reestablished through the vas since it may have in the meantime become closed downstream of the location where the fluid flow has been blocked.

SUMMARY OF THE INVENTION

It is accordingly a primary object of the present invention to provide methods and devices which will avoid these drawbacks.

It is in particular an object of the present invention to provide methods and devices which will assure flow of fluid through the vas deferens at all times, while at the same time being capable of achieving at least temporarily a condition where conception is reliably avoided.

Thus, it is an object of the invention to permit fluid to flow without interruption through the vas deferens at all times, while, when prevention of conception is desired, creating conditions where sperm in the fluid are acted upon in such a way that viable sperm cannot flow with the fluid beyond the vas deferens in numbers sufficient for achieving conception.

Thus, one of the more specific objects of the present invention is to provide for fluid in a vas deferens a path of flow which at least temporarily can be restricted to such an extent that while fluid can continue to flow through the vas deferens sperm are prevented from flowing with the fluid in numbers sufficient to achieve conception.

Also it is an object of the present invention to provide a method and device according to which it is possible to act on sperm in the vas deferens in such a way that they cannot be carried along with the fluid in the vas deferens in a condition where conception can be achieved.

It is also an object of the present invention to provide variable filtering methods and devices of general utility capable of adjustably restricting the flow path of a fluid in such a way that while fluid can continue to flow nevertheless at the same time even relatively minute components in the fluid can be filtered therefrom.

According to the invention there is provided a method and device according to which flow of fluid through a vas deferens is restricted to an extent which never completely interrupts the flow of fluid while at the same time when the flow is restricted sperm are acted upon in such a way that the fluid which flows beyond the vas deferens cannot carry with it viable sperm in numbers sufficient for achieving conception. These results can be achieved according to one of the features of the invention by variable filtering methods and devices which are of general utility.

BRIEF DESCRIPTION OF DRAWINGS

The invention is illustrated by way of example in the accompanying drawings which form part of this application and in which.

DESCRIPTION OF PREFERRED EMBODIMENTS

Referring first to FIGS. 1–4, there is illustrated therein one possible embodiment of a method and device according to the invention. Thus, FIG. 1 fragmentarily illustrates in a schematic sectional manner a vas deferens 20 which has an inner mucosa layer 22 and which is surrounded by the sheath 24. The surgeon will obtain access to the vas 20 and the sheath 24 surrounding the same, and the surgeon will introduce into the lumen of the vas 20 the elongated tubular instrument 26 which has a pointed end 28 so that at this pointed end it is capable of piercing easily through the wall of the sheath 24 and through the wall of the vas 20 into the interior thereof as illustrated. This elongated tubular instrument 26 is formed adjacent its pointed end 28 with an elongated slot 30 one edge 32 of which has the configuration shown most clearly in FIG. 2 so that if forms a scraping or cutting edge. With the instrument 26 introduced in the manner illustrated in FIG. 1, the surgeon will turn the instrument in the direction of the arrow shown in FIG. 2, so that the edge 32 will remove a layer of mucosa 22 at the location in the vas which is to receive the device of the invention. Thus, after having rotated the instrument 26 in the interior of the vas to remove the mucosa layer in the manner described above, the surgeon will remove the instrument 26.

Figures 2, 3, 4, 5:
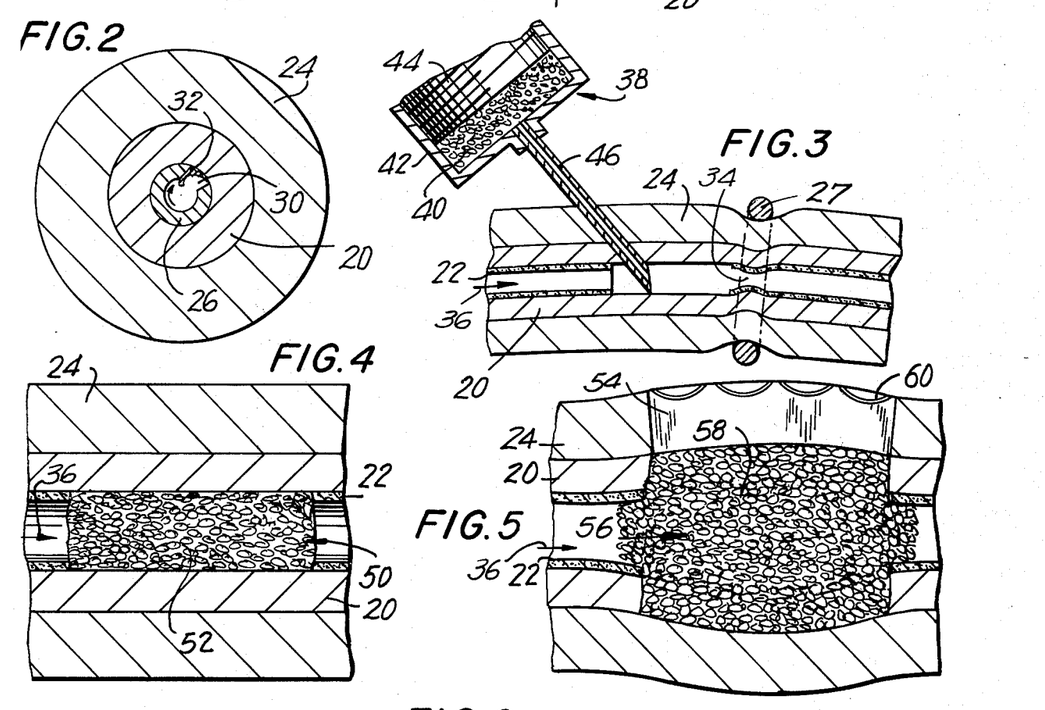
FIG. 2 is a transverse section of the illustration of FIG. 1 taken along line 2—2 of FIG. 1 in the direction of the arrows.
FIG. 3 is a schematic illustration of the manner in which bodies are injected into the vas deferens subsequent to the operations of FIGS. 1 and 2.
FIG. 4 is a schematic illustration of the vas deferens of FIG. 3 after the bodies have been injected into the same.
FIG. 5 is a schematic partly sectional illustration of a different method and device of the invention.

Then, the surgeon will place around the sheath 24 a suture 27 or other filamentary device for at least partly contracting the vas so that it will have a constricted portion 34 just downstream of the area where the mucosa 22 has been removed as indicated schematically in FIG. 3. It will be seen that the direction of fluid flow through the vas is indicated by the arrow 36 as flowing from the left toward the right, as viewed in FIG. 3.

A syringe 38 is provided with a supply 40 of small particles suspended in a suitable liquid such as a saline solution which is capable of being absorbed in the body. This syringe 38 has, for example, a barrel 42 into which a plunger 44 is threaded, and the barrel 42 has the elongated tubular needle 46 connected thereto and through which the supply 40 can be displaced by threading the plunger 44 further into the barrel 42. The pointed tip 48 of the needle 46 is introduced into the lumen of the vas 20 at the area from which the mucosa has been removed, as indicated in FIG. 3, and now the supply 40 contained in the barrel 42 will be displayed through the needle 46 into the vas in a manner shown in FIG. 3. Once the supply 40 of small particles suspended in saline solution, for example, has been displaced out of the syringe 38 into the interior of the vas, the needle 46 is removed, and the suture 27 or the like by providing the constricted portion 34 will prevent the body of particles from flowing beyond the area where they have been injected. In this way it is possible to situate in the interior of the lumen 20 a clump of small particles 50, as illustrated in FIG. 4. These particles 50 will engage each other to form extremely small passages through which fluid can flow, and tissue ingrowth will take place at the exterior of the group of particles 50 to maintain the latter in the position shown in FIG. 4. The suture 27 can be made of an absorbable material so that it will become absorbed after the clump or group 50 of particles reliably remains in the position shown in FIG. 4. Any saline solution or the like which is not absorbed will simply flow out from the spaces between the particles in response to flow of fluid through the vas in the direction of the arrow 36.

These particles 52 which form the group 50 illustrated in FIG. 4 are preferably magnetic and are compatible with the body. For example some of the particles 52 may be made of an alloy of platinum and cobalt, or they may take the form of exceedingly small ferromagnetic cobalt-alloy particles or the like which are covered with coatings of gold, so as to be compatible with the body. An alloy of platinum and cobalt is preferred since it is magnetic and at the same time does not require coating so as to be rendered compatible.

Figure 1:
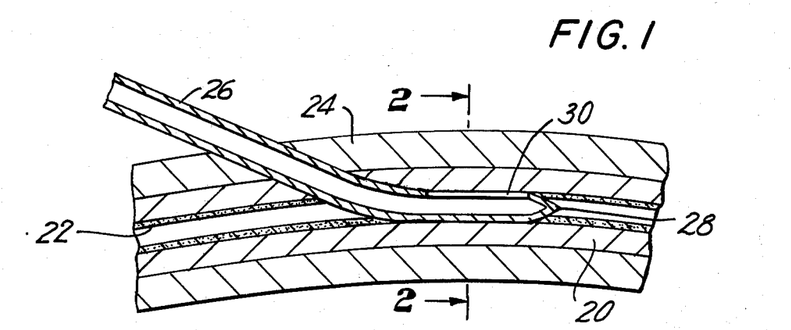
FIG. 1 is a fragmentary schematic sectional illustration of a vas deferens, shown at a greatly enlarged scale, with a structure utilized to remove mucosa from the lumen of the vas deferens.

Once a group of particles is situated in the vas through expedients such as that shown in FIGS. 1–3, a magnetic field is situated at the exterior of the sheath 24 adjacent the vas to act through magnetism on the magnetic particles 52 so as to create permanent magnets from the latter, and this will cause the magnets 52 to remain together in a clump 50 as illustrated in FIG. 4, and of course by the time the suture 26 or the like has been absorbed there will be sufficient ingrowth to retain the clump of group 50 of particles 52 in the position shown in FIG. 4. Thus, the removal of the mucosa layer in the manner shown in FIGS. 1 and 2 will greatly reduce the time required for tissue ingrowth to take place.

It will be noted that with the method of FIGS. 1–4 it is not required that the surgeon cut into the vas in order to have access to the interior thereof. All operations take place from the exterior of the sheath 24 which surrounds the vas, so that relatively little surgery is required.

Moreover, it is not essential to remove mucosa with a device as shown in FIGS. 1 and 2. For example it is possible also to insert a wire element one end of which is heated in a well known manner so that an operation similar to cauterizing takes place, and when such a heated element is displaced around the inner surface of the vas 20 it will also serve effectively to remove the layer of mucosa so as to hasten ingrowth with respect to the group of particles 50 introduced by way of the syringe 38 in the manner described above and shown in FIG. 3. Moreover, it is possible to use vibratory or reaming procedures or both in order to remove the mucosa. Thus it is possible to form an incision through which access may be had to the interior of the vas for introducing into the latter a reamer which can remove the mucosa and this reamer can be vibrated to bring about the mucosa removal.

The result of these procedures is to situate in the lumen 20 the device formed by the group 50 of particles 52 which magnetically remain in engagement with each other to provide a restricted flow path through the vas.

By properly choosing the size of the particles 52 and the magnitude of the magnetic force applied thereto, it is possible to control in a precise manner the extent to which the fluid can flow through the group 50 of particles 52.

For example, the particles 52 while being preferably made of an alloy such as an alloy of platinum and cobalt have a size which will depend upon the materials and shapes as herein described, and this size may be on the order of 50 microns. Thus when these particles are viewed with the naked eye they appear as a powder. However they will remain reliably together in a group as a result of the magnetic attraction of the particles with respect to each other, and they will provide a controlled flow.

Thus it is possible for fluid to flow through and beyond the group 50 of particles 52, so that at no time is there a complete interruption of flow of fluid through the vas. As a result it is possible for a male individual to maintain the desirable supply of hormones as well as to maintain the passage through the vas open downstream of the group 50 of bodies 52.

At the same time because of the above size of the particles and the fact that they are held in engagement with each other with a predetermined magnetic force, it is not possible for sperm to flow past the group 50 of bodies 52. On the average sperm will have at one end a relatively enlarged region the width of which is on the order of 3 microns, the length of which is on the order of 5 microns, and the thickness of which is on the order of 1 micron. This enlarged region is joined to one end of a relatively long tail which has a length on the order of 60 microns. Therefore with the above procedures to place a device formed by the group 50 of the bodies 52 in the vas, there will be a reliable prevention of flow of sperm together with other fluid in the vas beyond the device formed by the group 50 of bodies 52. The sperm which are retained will of course be absorbed into the body. In fact sperm absorption takes place all the time in any event in a normal male. Thus through these procedures there is never a time when a flow of fluid is completely interrupted in the vas, while at the same time conception can be reliably avoided.

FIG. 5 shows a variation of the method and device of the invention according to which the sheath 24 is cut by the surgeon so as to form an elongated slit 54 as illustrated in FIG. 5. At this slit the sheath can be separated from the vas 20 so as to give access to the latter, and now a section of the vas is removed. The group 56 of bodies 58 may be substantially identical with the group 50 except that in this case the bodies are placed directly in the sheath 24 in the space from which the vas section has been removed. The sheath 24 is then returned to its initial condition surrounding the group of bodies with the slit being closed, as by the sutures 60, and the tight pulling of the sheath around the group of particles in this way serves to maintain the particles 58 in the position indicated in FIG. 5 so that with this embodiment it is the returning of the sheath to its initial condition which is relied upon to exert an inwardly directed radial pressure which will hold the bodies 58 in the position shown in FIG. 6. These bodies 58 will act in the same way as the bodies 52 in order to achieve the results set forth above.

Figure 6:
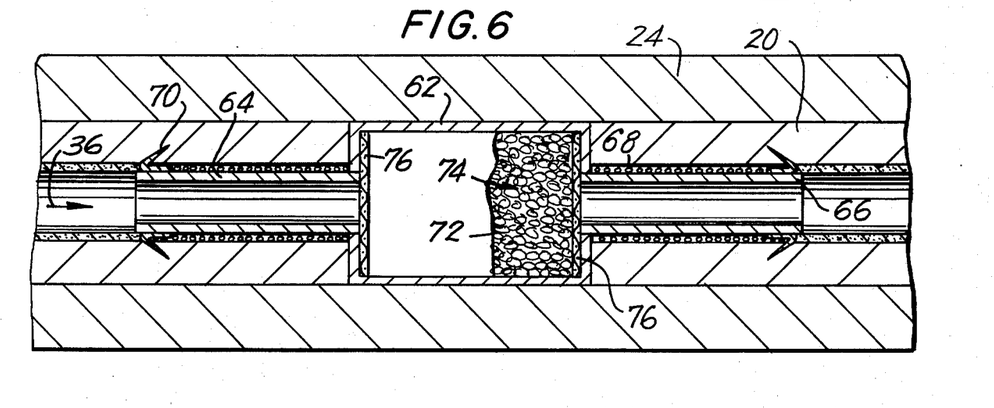
FIG. 6 is a schematic longitudinal sectional illustration, at a greatly enlarged scale, of a further embodiment of a method and device of the invention.

According to the embodiment of the invention which is illustrated in FIG. 6, an enclosure 62 is introduced into the vas 20 through known surgical procedures. The enclosure 62 has opposed tubular extensions 64 and 66 which respectively form an inlet and outlet directing fluid into and out of the enclosure 62. These components 64 and 66 as well as the enclosure 62 are made of any suitable material compatible with the vas such as, for example, gold. Moreover, the tubular inlet 64 and outlet 66 are surrounded with gold wire 68 or a suitable porous matrix or the like to form a tissue ingrowth means, and also suitable flexible barbs 70 are provided to dig into the wall of the vas 20 for reliably retaining the entire device shown in FIG. 6 in the position illustrated in the path of flow of fluid through the vas in the direction of the arrow 36. Before the enclosure 62 is introduced into the vas, a group 74 of particles 72 is placed in the enclosure 62. This is done, for example, by first removing one of the end walls of the enclosure 62, introducing the particles 74, and then replacing the end wall which may be fused or welded in any way to completely close the enclosure 62.

Moreover, the ends of the tubular inlet 64 and tubular outlet 68 which are joined to the end walls are closed by suitable porous closures 76 which provide passages large enough for fluid to flow through these closures 76 but small enough to retain the particles 72 in the interior of the enclosures 62. Thus, these closures 76 may be made by covering small particles with a metal which is fused together to form what amounts to a porous sintered body which can then be fused or welded to the inner surface of each end wall of the enclosures 62 in a manner shown in FIG. 6. It is also possible through nuclear bombardment to achieve exceedingly fine pores passing through layers of a sheet material which can be joined in any suitable way to the inner surface of each end wall of the enclosure 62 for also permitting fluid to flow through the enclosure while retaining the particles 72 therein. These particles 72 may have the same construction as the particles 52 or the particles 58. Closures 76 form screens having openings each of which has a dimension on the order of 40 microns. Thus, once the enclosure 62 together with the remaining parts connected thereto are introduced into the vas, it is possible to cause the particles 72 to a group together forming a group 74 situated in a clump at one or the other of the ends of the enclosure 62 in the manner illustrated in FIG. 6. In this case also by regulating the force of magnetism which is used for attracting the particles to each other, a controlled passage will be provided for permitting fluid to flow through the vas while preventing sperm from being carried along with the fluid. By properly selecting the external magnetic flux it is possible to control the size of the passage through which the fluid can flow, so that a variable control for flow of fluid is provided in this way.

However, with the embodiment of FIG. 6, as contrasted with the embodiments of FIGS. 4 and 5, it is possible to demagnetize the particles 72 in a well known manner as by exposing the particles to a suitable field of alternating flux, and once these particles are demagnetized they are capable of moving freely about in the enclosure 62, forming a mass of a relatively fluffy consistency providing very little resistance to flow of fluid. Under these conditions, it is possible for sperm to travel through the pores in the relatively small thickness of the closures 76 as well as through the loose group of particles 72 so that with the arrangement of FIG. 6 a reversible prevention of conception is very effectively and reliably achieved without ever completely interrupting the flow of fluid through the vas.

Of course, it would be possible to obtain similar results with the embodiments of FIGS. 4 and 5 by demagnetizing the particles. This would only require the demagnetized particles to be released with the ejaculate, and several ejaculations may be used over a period of a week or two in order to completely flush out the particles, thus providing a return to the capability of conception with an arrangement as shown in FIGS. 4 and 5. Also with arrangements as shown in FIGS. 4 and 5 it is possible by first demagnetizing the particles and then providing a magnetic attraction only away from the axis of the lumen radially toward the inner surface thereof to arrange the magnetic particles in a ring forming a ring of magnetized particles defining an opening through which the fluid can readily flow.

The great advantage of a procedure of this latter type as well as the method and apparatus of FIG. 6 resides in the fact that, in contrast to completely flushing the particles out of the vas, the particles are maintained therein so that when it is again desired to achieve a conception-preventing state, the particles can be returned to the condition shown in FIGS. 4-6.

As has been indicated above, by controlling the extent of magnetic force applied to the particles it is possible to control the density of the filter which is provided by the group of particles which are magnetically attracted to each other. These arrangements are of general utility in controlling flow of fluid.

As was pointed out above, expedients as shown in FIG. 6 are of general utility in controlling fluid flow by controlling the extent of magnetic force which is applied to the particles which in effect form a filter through which fluid can flow in a controlled manner.

Figure 7:
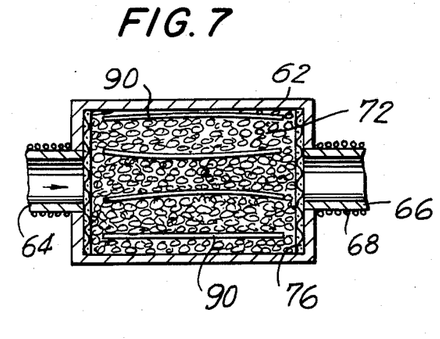
FIG. 7 is a schematic sectional elevation of a further embodiment of a method and device of the invention which is of general utility.
Figure 8:
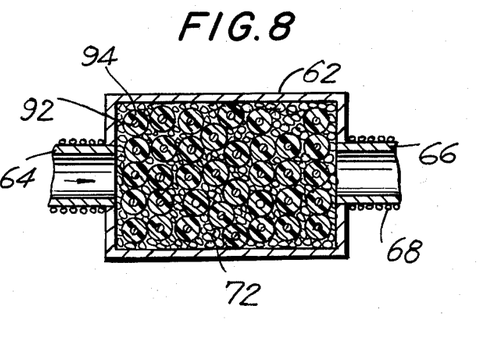
FIG. 8 is a sectional illustration schematically showing a further embodiment of a method and device of the invention which is of general utility.

Variations of this latter type of arrangement are illustrated in FIGS. 7 and 8. Thus according to the embodiment shown in FIG. 7, the structure may be identical with that of FIG. 6 except that in the enclosure 62 the particles 72 have interspersed therewith elongated fine hairlike springy elements 90 which with a suitable spring force maintain the particles 72 spaced from each other providing a relatively free flow path. Now when the particles 72 are magnetized they will be attracted toward each other in opposition to the force of the spring elements 90 so that an extremely precise control of the rate of fluid flow is achieved.

Furthermore, an arrangement as shown in FIG. 8 can be provided where the enclosure 62 contains particles 92 which may be identical with particles such as the particles 52, 58, or 72. However in this case at least some of these particles 92 are each surrounded by a layer 94 of a suitable resilient elastic plastic material, and in fact the size of these particles 92 together with the layers 94 are large enough so that it is not required to provide porous retaining closures at the ends of the inlet 64 and outlet 66. If such closures are required they can have much larger openings because the sizes of the particles 92 are considerably increased by the resilient compressible layers 94.

When with this arrangement, the particles 92 are demagnetized the springy force of the layers 94 will urge them apart from each other to provide relatively open free passages through which fluid can flow with little resistance. On the other hand it is possible to apply magnetic force to the particles 92 so as to cause them to magnetically attract each other in opposition to the springy force of the coverings 94 so as to restrict the fluid flow to a predetermined extent thus achieving the desired results of a variable flow filter capable of having the passage of fluid therethrough closely regulated. In the case of a vas deferens of course it is desirable to cause the particles 92 to attract each other sufficiently to provide a flow path small enough to retain sperm while permitting the other fluid in the vas to flow through to achieve the results set forth above. However it is clear that the variable filter arrangements of FIGS. 7 and 8 and the fluid control arrangement of FIG. 6 are of general utility and can be used for variable filter or flow control procedures for purely commercial purposes in many different industries where variable flow filters or precise regulation of fluid flow are required.

Figure 9:
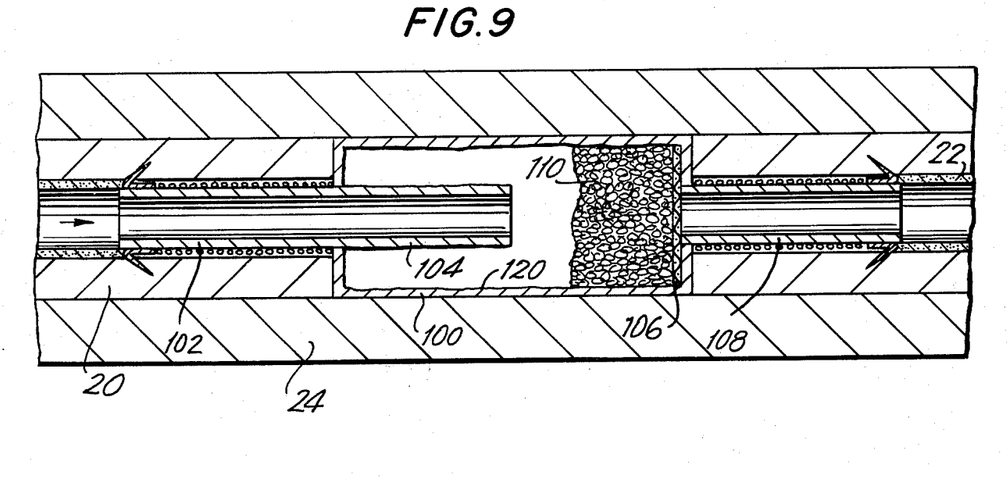
FIG. 9 is a schematic longitudinal section of a method and device of the invention which differs from those of FIGS. 1–8 and which also enables the desired results to be achieved.
Figure 10:
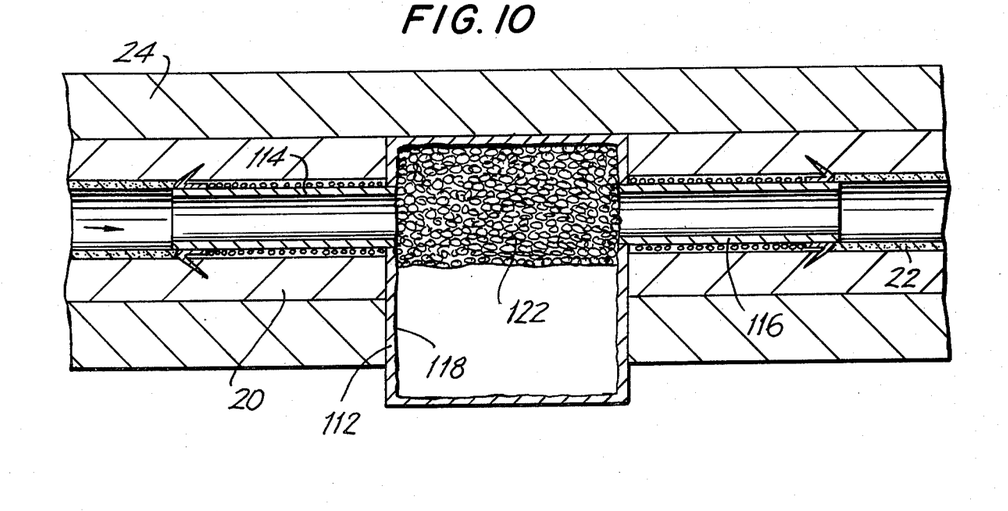
FIG. 10 is a fragmentary longitudinal schematic sectional elevation of a still further embodiment of a method and device of the invention.

Further variations are possible as shown in FIGS. 9 and 10. Thus in FIG. 9 there is situated in the vas 20 an enclosure means 100 which may be identical with the enclosure 62, including all of the components connected to the latter except that in this case the inlet 102 which corresponds to the tubular inlet 64 is longer and has an elongated portion 104 extending along the hollow interior of the enclosure 100 in a manner illustrated in FIG. 9. This construction requires only one screen means 106 situated at the region of the outlet element 108 which corresponds to the tubular outlet 66. Thus this element 106 is a simple plate which has been bombarded or otherwise treated to have small openings through which the fluid can flow while retaining the particles 110 which may be identical with any of the above magnetic particles. When this device has been introduced into the vas in the manner shown in FIG. 9, the particles 110 are magnetized and positioned at the location shown in FIG. 9 at the top end of the enclosure 100 so as to permit fluid to flow while retaining sperm. On the other hand, when it is desired to reestablish a conception-enabling condition, the particles 110 are partially demagnetized through any of the expedients referred to above and moved toward the other end of the enclosure 100 surrounding the tube 104, by displacing the magnetic field toward this other end of the enclosure, so that now a relatively unrestricted flow will be achieved and of course it will be possible for sperm to flow through the openings of the screen 106 because of the small thickness of the latter. The magnetic force can be intensified at this other end of the enclosure for maintaining the particles in their position surrounding the tube 104.

The arrangement of FIG. 10 is substantially identical with those referred to above except that in this case the enclosure 112 extends to one side of the tubular inlet 114 and the tubular outlet 116 which may be identical with the tubular inlet 64 and the tubular outlet 66. In this case by applying the magnetic force to one side of the sheath 24, the clump of particles 116, which may be identical with any of the above particles, is situated in a rigid clump where they attract each other and restrict the flow through the vas to such an extent that the sperm will be retained while fluid can continue to flow through. On the other hand, the particles 116 can be at least partially demagnetized and then the field can be transferred to the other side, so that the entire clump can be magnetized and will remain in a position completely to one side of the passage through the inlet 114 and outlet 116 so that a completely unrestricted flow can be achieved in this way with a full reversal. If desired suitable irregularities such as an inner roughened surface 118 can be provided at the inner surface of the enclosure 112 to contribute toward retaining the particles 116 either in their blocking or non-blocking condition, and of course similar irregularities 120 can be provided at the inner surface of the enclosure 100 and around the exterior of the inner extension 104 for contributing to retaining the particles in a desired location.

It is apprent that the methods and devices illustrated in FIGS. 6–10 permit complete reversal between a conception-preventing condition and a conception-enabling condition, with a further return from a conception-enabling condition to a conception-preventing condition whenever desired. However, these arrangements also may be used in those cases where it is felt that the sperm which are prevented from flowing with the fluid when the parts have the conception-preventing condition will block the flow after becoming accumulated over a long period of time during which there may in some cases be a possibility of non-absorption of sperm back into the body at a rate sufficient to reliably maintain the desired flow of fluid at all times. In such cases, the magnetic bodies may be demagnetized to reestablish full flow through the vas, and while avoiding sexual intercourse for a period of a few weeks or a month, it is possible to completely flush out any sperm which have accumulated, and thereafter it is possible to apply again a magnetic force which will return the magnetic bodies to the condition where they form permanent magnets attracting each other to provide the restricted flow which will retain sperm while permitting the fluid which otherwise would carry the sperm to flow through the vas.

Moreover, it is not essential to utilize bodies magnetically attracted to each other to achieve the results desired. Various additional methods and devices of the invention are illustrated in FIGS. 11–15.

Figure 11:
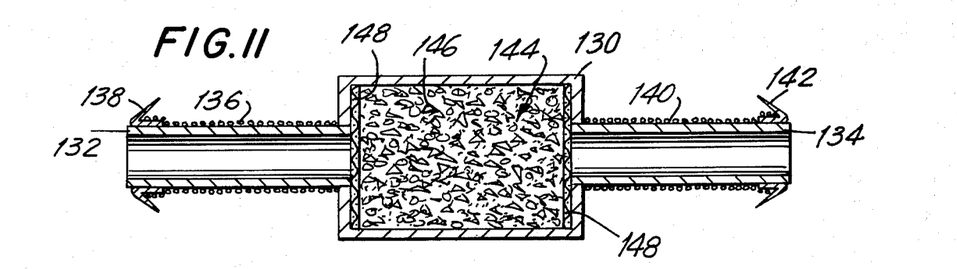
FIG. 11 is a schematic sectional elevation of a further embodiment of a method and device of the invention.

Thus, FIG. 11 shows an enclosure 130 which may be identical with the enclosure 62 and which may also have an identical tubular inlet 132 and a tubular outlet 134, respectively, corresponding to the tubular inlet 64 and the tubular outlet 66. The inlet 132 is surrounded by a tissue ingrowth means 136 and carries the flexible barbs 138, and in the same way the outlet 134 is surrounded by a tissue ingrowth means 140 and carries the flexible barbs 142. Thus construction can readily be introduced into the vas in a well known manner, assuming a position as illustrated for the enclosure 62 in FIG. 6.

However, the interior of the enclosure 130 contains a group 144 of bodies 146 which are retained in the enclosure 130 by way of the screens 148 covering the open ends of the tubular inlet 132 and outlet 134 which are joined to the opposed end walls of the enclosure 130. These screens 148 may be formed by fusing together suitable bodies forming in effect a sintered closure which is fused or welded to the inner surfaces of the end walls of the enclosure 130 in the manner described above, but in this case the passages through the screens 148 can be much larger than in the case of FIG. 6. The bodies 146 also can be somewhat larger than the magnetic particles or bodies referred to above. These bodies 146 are preferably diamond particles which are of a relatively small size but which have sharp points and edges. Therefore with this arrangement the fluid can flow through the vas with much less resistance to flow than with the above embodiments when the magnetic bodies are magnetically attracted to each other. However, because of the sharp edges and points provided by the diamond particles 146, which are fully compatible with the body, sperm flowing through the enclosure 130 will become damaged, by being cut or otherwise injured so that with an arrangement as shown in FIG. 11 viable sperm cannot flow with the fluid through the vas in numbers sufficient to achieve conception. Thus, through an arrangement as shown in FIG. 11 it is also possible to prevent conception while maintaining flow of fluid through the vas.

Figure 12:
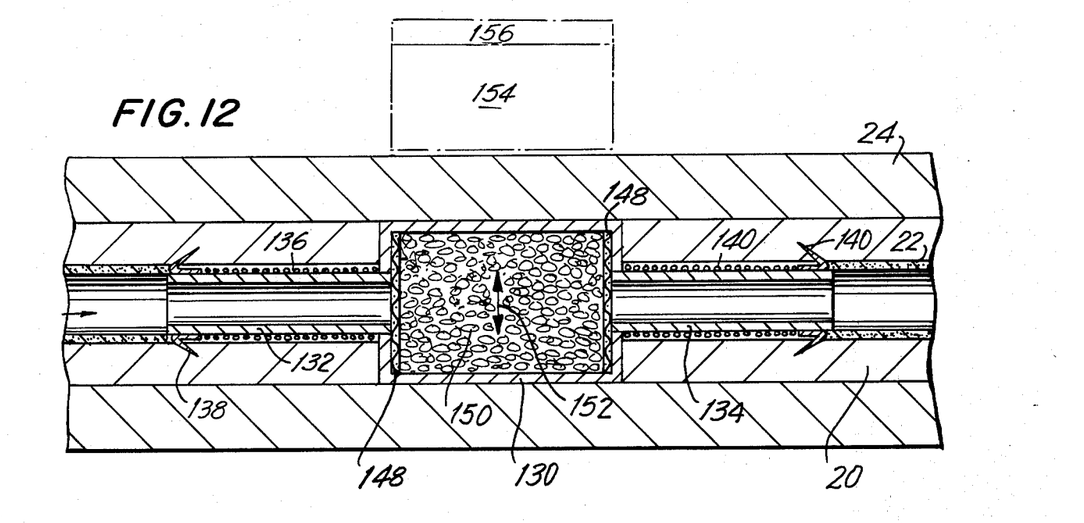
FIG. 12 is a fragmentary sectional elevation schematically illustrating a still further embodiment of a method and device of the invention.

With an arrangement as shown in FIG. 12, the enclosure 130 is identical with that of FIG. 11 and has identical parts connected thereto, including the screens 148 at the open ends of the inlet 132 and the outlet 134 which are joined to the opposed end walls of the enclosure 130. In this case any solid electrically conductive, preferably magnetic particles 150 can be situated in the enclosures 130. The particles 150 are of a relatively small size and are situated in the enclosure 130 in an amount sufficient to enable the particles 150 to move freely about, as indicated by the double-headed arrow 152.

In this embodiment a vibrating means 154 is maintained at the exterior of the body of the individual by being held in any suitable enclosure outside of and adjacent the skin, in the region of the structure shown in FIG. 12. For example the vibrating means 154 may be carried about in a trouser pocket, if desired. This vibrator 154 is in the form of any suitable generator of alternating current or of an alternating magnetic field driven by a small battery 156. Through the battery 156 it is possible to act on the unit 154 to provide small microvibrations in particles 150. These minute high frequency microvibrations are not felt by the individual. However, they do result in movement of the bodies 150 sufficient to injure sperm in the fluid flowing through the vas. Because the bodies 150 which vibrate at high frequency with microvibrations impinge against the sperm, the latter are damaged and placed in a condition where conception cannot be achieved, so that with the embodiment of FIG. 12 it is also possible to prevent the fluid which flows through the vas from carrying with it viable sperm in numbers sufficient to achieve conception.

Figure 13:
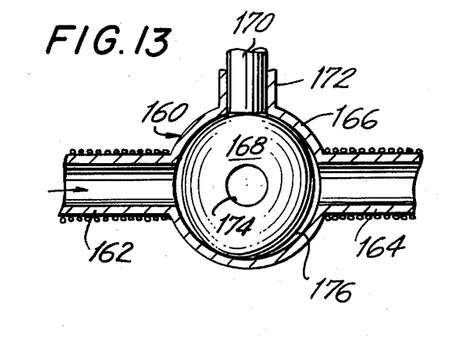
FIG. 13 is a fragmentary schematic sectional elevation of a valve constructed in accordance with the invention and shown at a greatly enlarged scale in FIG. 13.

According to the embodiment of the method and device of the invention which is illustrated in FIG. 13, a valve 160 is introduced into the vas. This valve may be for the most part of a well known construction having tissue ingrowth means and barbs at the inlet 162 and outlet 164 of the valve 160 which has a housing 166 surrounding the valve member 168. The valve member 168 is capable of being turned either to a position shown in FIG. 13 or to a position displaced 90° from the position shown in FIG. 13 by turning the stem 170 which is fixed to the valve member 168 and which extends through the tubular neck 172 of the housing 166. When the valve member 168 is turned through 90° about the axis of the stem 170 from the position shown in FIG. 13, a throughbore 174 of the valve body 168 is in line with the tubular inlet 162 and outlet 164 so that fluid can flow freely through the valve which now is in its fully open position.

According to the invention the valve body 168 is not completely round or fully spherical at its exterior surface, while the inner surface of the housing 166 is in fact part of a perfect sphere. Thus, the body 168 is initially made in an out-of-round configuration and may, for example, be covered with a layer of a suitable wax before the housing 166 is deposited around the body 168 in a well known manner. Thereafter the wax can be melted out through the inlet 162 or the outlet 164, so as to leave an arrangement as shown in FIG. 13 on a greatly enlarged scale. With this arrangement when the valve 168 is turned to the illustrated condition which otherwise, in an ordinary valve, would be the completely closed position of the valve, there is instead a minute gap 176 providing a predetermined clearance between the housing 166 and the valve body 168. Through this gap 176 of predetermined magnitude it is possible for fluid in the vas to flow through the valve while the gap 176 is restricted enough to prevent sperm from flowing through with the fluid. Thus, the arrangement of FIG. 13 provides a valve which either is in a partially open, actually almost fully closed, position, or in a fully open position, and in the fully open position substantially unrestricted flow is provided while in the partially open position flow is restricted to such an extent that sperm cannot continue to flow with the fluid through the vas, so that in this way it is also possible to achieve the results of the invention.

Figure 14:
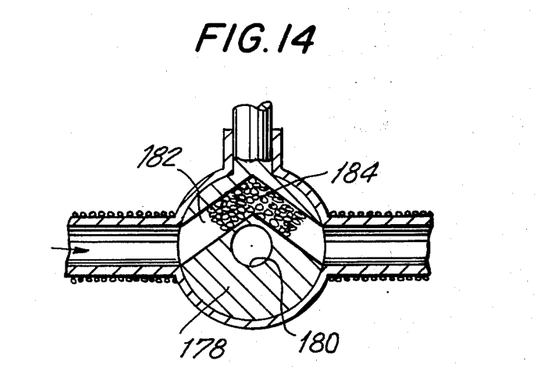
FIG. 14 is a longitudinal sectional elevation fragmentarily illustrating a further embodiment of a valve according to the invention, the structure of FIG. 14 also being shown at a greatly enlarged scale.

Instead of an arrangement as shown in FIG. 13, it is possible to use an arrangement as shown in FIG. 14 where all of the parts are identical with that of FIG. 13 except that the valve body 78 in this case has a pair of passages therethrough. One of these passages is the diametrical through-bore 180 which when aligned with the inlet and outlet of the valve provide unrestricted flow therethrough. This passage 180 extends between legs of a V-shaped passage 182 which is shown in FIG. 14 in line with the inlet and outlet of the valve. In this V-passage 182 there is located a clump of bodies 184 providing the restricted flow which prevents sperm from accompanying the fluid through the valve. As a result when the device of FIG. 14 is situated in the vas, it is possible to place the valve in one position where unrestricted flow is provided through the bore 180 and in the position shown in FIG. 14 where the flow through the vas in restricted by the particles 184. Of course these particles need not be magnetic. They can be placed in the passage 182 and held together by sintering or the like so as to provide a controlled restricted flow through the passage 182. Naturally, it is possible, if desired, to provide magnetic bodies which can be magnetically attracted to each other to provide the filtering clump 184 which controls the fluid flow in such a way that sperm cannot accompany the fluid. It will be noted that in the case of FIG. 14, as is the case with FIG. 13, complete reversals can be repeatedly provided between conception-enabling and conception-preventing conditions.

Figure 15:
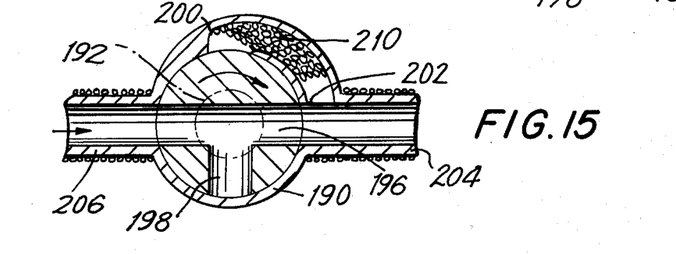
FIG. 15 shows yet another construction of a valve according to the invention, FIG. 15 illustrating this valve a greatly enlarged scale in a schematic manner.

With an arrangement as shown in FIG. 14, the V-shaped passage 182 affords only a limited space for accommodating the filtering structure 184, and an arrangement as shown in FIG. 15 may be preferred inasmuch as this arrangement will provide a much larger space for accommodating a larger group of bodies to provide the restricted flow. Thus, FIG. 15 shows a valve with the section of FIG. 15 being taken in a plane through the valve housing 190 perpendicular to the axis of the stem 192 which is shown in phantom lines in FIG. 15. The valve body 194 is formed with a T-shaped bore having a through-bore portion 196 and a leg 198 communicating with the through-bore portion 196. The housing 190 is formed with a passage 200 which can be made much larger than the passage 182 simply by providing a suitable thickness for the housing 190 and forming in the wall thereof the relatively large passage 200 arranged as illustrated so that one end 202 of the passage 200 communicates with the outlet 204 of the valve shown in FIG. 15. This outlet 204 is located at the side of the housing 190 diametrically opposed to the inlet 206, and of course the outlet 204 and the inlet 206 carry at their exteriors suitable tissue ingrowth means and flexible barbs as described above.

Within the passage 200, which communicates with the interior of the housing 190 at a part thereof diametrically opposed to the leg 198 of the T-bore, with the position of the parts shown in FIG. 15, is located a group of bodies 210 which are clustered together either by sintering or by magnetic attraction or the like so as to provide a relatively large filter having a flow path which can be precisely regulated to provide the desired restriction which will retain sperm but permit fluid without sperm to flow through.

Figures 16, 17:
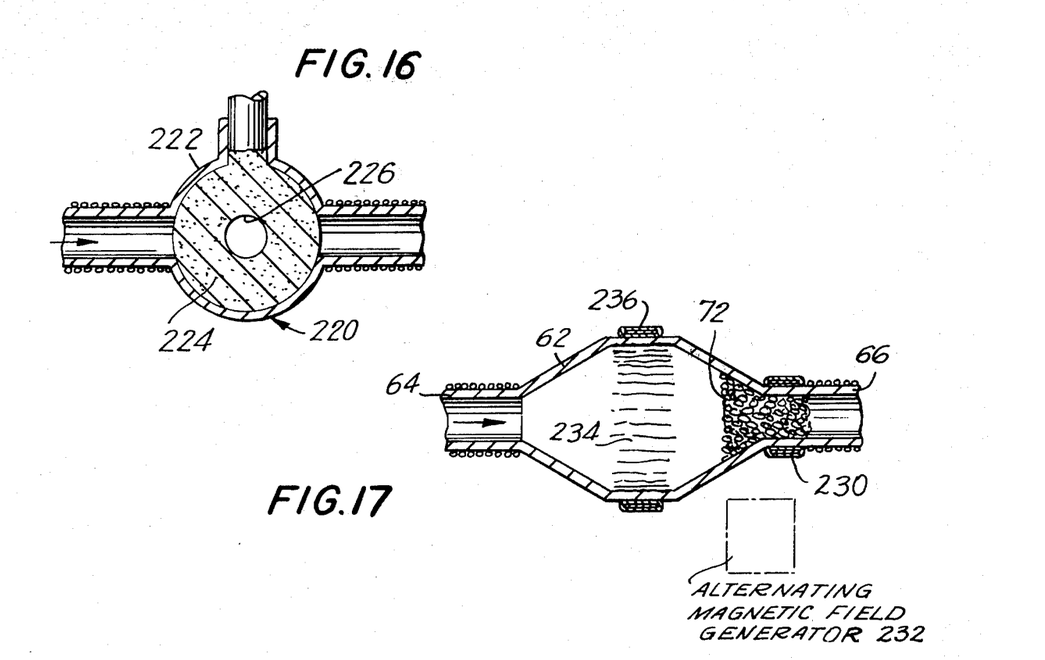
FIG. 16 is a fragmentary schematic sectional elevation of a further embodiment of a valve in accordance with the invention.
FIG. 17 is a fragmentary schematic sectional elevation of yet another embodiment of a device according to the invention.

With this arrangement when the valve has the position shown in FIG. 15, the throughbore portion 196 communicates with the inlet 206 and the outlet 204 so that unrestricted flow is provided. However, by turning the valve body 194 through 90° in a clockwise direction from the position shown in FIG. 15, it is possible for the leg 198 of the T-bore to communicate with the inlet 206, while the throughbore 196 will at this time communicate only with the passage 200, so that with the valve body 194 in this position the fluid entering through the inlet 206 will be deflected through 90° to the passage 200 and will be compelled to flow through the group of bodies 210 before reaching the outlet 204. As a result it is possible to provide a relatively large filter 210 providing the required, precisely controlled restriction which will retain the sperm but permit the fluid to flow through. A further embodiment of a valve according to the invention is illustrated in FIG. 16. In this embodiment the valve 220 has a housing 222 in which a sintered valve member 224 is turnable, this sintered spherical valve member 224 being formed with a throughbore 226 aligned with the inlet and outlet when the valve is in its fully open position. In the position shown in FIG. 16, the sintered valve member 224 has a porosity between its sintered particles sufficiently great to enable liquid to flow through the sintered body from the inlet to the outlet of the valve while preventing sperm from being carried along with the fluid.

According to the embodiment of the invention shown in FIG. 17, the construction may be substantially identical with that of FIG. 6, for example, except that the enclosure 62 need not contain the porous screen 76. The paprticles 72 are rendered magnetic by exposure to the field of a permanent magnet of sufficient strength and due to their magnetic attraction, the particles 72 will remain in the position shown in FIG. 17 at the region of the outlet 66. This magnetic attraction eliminates the necessity for a screen. However, a ring 230 of magnetically responsive material may be situated around the outlet 66 next to the right end of the enclosure 62 for contributing to the maintaining of the magnetic particles at the outlet without using a screen. This ring may be made of an inner layer of gold, an intermediate layer of nickel and an outer layer of gold, with these layers being extremely thin, so that the thickness of the structure is not materially increased by the ring while at the same time it will have the magnetically responsive behavior which is desired.

When it is desired to permit fluid to flow through the device of FIG. 17 with sperm, the particles 72 are exposed to an alternating magnetic field provided by way of an alternating magnetic field generator 232 shown in phantom lines. As a result of the action of the alternating magnetic field, the particles 72 move freely about and can be directed toward the central region of the enclosure 62 between the ends thereof where the inner surface of the enclosure 62 may be roughened, if desired, as indicated at 234. For this it is only necessary to create with a suitable permanent or electro magnet a magnetic field of sufficient strength at the central region of enclosure 62. This magnetic field will attract and displace the particles toward the left, as viewed in FIG. 17. Once the particles 72 have been displaced in this way to the central region of the enclosure 62, the operation of the generator 232 is terminated and the central magnetic field can be eliminated. The particles which still retain their magnetism will attract each other and remain stably at the location between the end walls of the enclosure 62. For this purpose a suitable magnetically responsive ring 236 can be carried by the enclosure 62 surrounding the latter. This ring 236 also can be made of an inner thin layer of gold which in turn carries a thin layer of nickel which in turn is covered by an outer layer of gold so that the construction of the ring 236 is substantially the same as the construction of the ring 230. As a result, the particles 72 will spread themselves around the inner surface of the enclosure at the region of the ring 236 to provide through the interior of the enclosure an opening sufficiently large for substantially unrestricted flow of fluid. Through the unit 232 it is possible to achieve a predetermined degree of demagnetization, the stronger the alternating field the greater the demagnetization, with this demagnetization being made sufficiently great so that the particles will loosen up and move away from the location in the outlet 66 toward the region of the ring 236 to which they are attracted by the above magnetic field. It is thus possible to provide a sufficiently strong magnetic attraction in the particles which attract each other while being spread around the interior of the enclosure at the region of the ring 236. Thus, with this embodiment it is possible to achieve the desired results without demagnetizing the bodies 72.

It is thus apparent that with all of the above-described methods and devices of the invention it is possible to achieve the desired result of never interrupting flow of fluid through the vas so that the vas will reliably remain open even downstream of the location of the device of the invention, while at the same time the required supply of hormones and the like will be assured. However, it is possible because of the restriction provided with the method and device of the invention to prevent viable sperm from flowing through the vas with the fluid in numbers sufficient to achieve conception. Moreover, the principles of the invention have applicability beyond the use as a conception-preventing arrangement. Thus as was described above it is possible to use devices and methods of the invention for general variable filtering purposes as well as for providing variable flow devices, and of course it is possible also to use the methods and devices in other parts of the body.

What is claimed is:

1. In a method for at least temporarily preventing the ejaculate of a male from containing viable sperm in numbers sufficient for conception, the steps of implanting in a vas deferens a filter means for at least temporarily providing for the flow of vas fluid through the vas deferens a selective flow path across which the filter means extends and along which the filter means at least in part by filteration provides for the sperm a path of flow along which said filter means acts, said filter means including means preventing in a mechanical, non-chemical manner viable sperm from being carried along with the fluid in numbers sufficient for conception, and securing the thus-implanted filter means to the vas deferens for remaining at a predetermined location of the vas deferens.

2. In a method as recited in claim 1, said filter means including a group of bodies which form a restricted path permitting fluid in the vas to flow past the bodies while said bodies act in said mechanical, non-chemical manner on the sperm in the fluid to prevent the fluid which flows beyond the group of bodies from containing the viable sperm in numbers sufficient for conception.

3. In a method for at least temporarily preventing the ejaculate of a male from containing viable sperm in numbers sufficient for conception, the step of at least temporarily providing for the flow of fluid through a vas deferens a selective flow which prevents viable sperm from being carried along with the fluid in numbers sufficient for conception, said step including situating in the flow of fluid in a vas deferens a group of bodies which form a restricted path and permit fluid in the vas to flow past the bodies while acting on the sperm in the fluid to prevent the fluid which flows beyond the group of bodies from containing viable sperm in numbers sufficient for conception, and holding the bodies together to form therefrom a clump of bodies which engage each other and providing for the bodies a size and shape causing the bodies to act as a filter which will prevent sperm from travelling with fluid beyond the filter.

4. In a method as recited in claim 3 and wherein the bodies are made of a magnetic material, and including the step of magnetizing the bodies to a preselected degree so that they act as magnets attracting each other with predetermined force which can be regulated.

5. In a method as recited in claim 2 and including the step of injecting the group of bodies into the interior of the vas deferens.

6. In a method as recited in claim 5 and including the step of removing from the interior of the vas deferens, prior to injecting the group of bodies into the latter, a layer of mucosa at the location where the bodies are situated.

7. In a method as recited in claim 6 and including the step of reducing the size of the vas deferens just beyond the location where the group of bodies is injected to maintain the group of bodies in the vas deferens at the location where mucosa has been removed at least for a time sufficient for tissue ingrowth to take place at the exterior surface of the group of bodies.

8. In a method as recited in claim 3 and including the steps of cutting through the sheath which surrounds the vas deferens, then removing a section of the vas deferens and introducing into the space occupied by the removed section of the vas deferens bodies in an amount sufficient for the bodies to form said clump, and then fastening the sheath around said bodies with the sheath engaging the clump with a pressure sufficient to retain the bodies at the location where they have been placed within the sheath.

9. In a method for at least temporarily preventing the ejaculate of a male from containing viable sperm in numbers sufficient for conception, the step of at least temporarily providing for the flow of fluid through a vas deferens a selective flow which prevents viable sperm from being carried along with the fluid in numbers sufficient for conception, said step including situating in the flow of fluid in a vas deferens a group of bodies which form a restricted path and permit fluid in the vas to flow past the bodies while acting on the sperm in the fluid to prevent the fluid which flows beyond the group of bodies from containing viable sperm in numbers sufficient for conception, the bodies being at least partly of a magnetic material, and including the steps of situating the bodies in an enclosure which is connected to the vas deferens for directing fluid therein through the interior of the enclosure and past the bodies situated therein, and acting on the magnetic properties of the bodies for placing them either in a conception-preventing condition where the bodies permit fluid to flow past the bodies while acting as a filter to prevent sperm from flowing past the bodies or in a conception-enabling condition where the bodies permit fluid in the vas with living sperm therein to flow freely past said bodies.

10. In a method as recited in claim 9 and including the steps of magnetizing the bodies to cause them to magnetically attract each other for assuming said conception-preventing condition and demagnetizing the bodies for permitting them to move apart from each other for assuming the conception-enabling condition, said enclosure being large enough to provide for relatively free movement of the bodies with respect to each other when the bodies are demagnetized.

11. In a method as recited in claim 9 and wherein the bodies are made at least partly of a magnetic material and including the steps of urging the bodies apart from each other with a spring force for placing the bodies in the conception-enabling condition and magnetizing the bodies to draw them together by magnetic attraction in opposition to the spring force to an extent sufficient for preventing sperm from being carried by fluid past the bodies while the fluid without the sperm can flow beyond the magnetized bodies.

12. In a method as recited in claim 9 and wherein the enclosure is large enough with respect to the group of bodies to accommodate them either in the path of fluid flow for assuming the conception-preventing condition or beyond the path of fluid flow for assuming the conception-enabling condition, and acting magnetically on the bodies to place them in one or the other of said locations.

13. In a method as recited in claim 2 and wherein the bodies are situated in an enclosure which is introduced into the vas deferens and through which the fluid flows past the bodies, and situating in said enclosure a group of bodies which have surfaces which are irregular and provided with sharp edges, points, and the like for injuring sperm carried by fluid in the vas for preventing the fluid which flows past the bodies from having therein undamaged sperm in numbers sufficient for conception.

14. In a method as recited in claim 2 and wherein the bodies are situated in an enclsure which is connected to the vas for compelling fluid to flow through the enclosure past the bodies, and vibrating the bodies in the enclosure to an extent sufficient to act on sperm with vibrating bodies to render the sperm ineffective for conception.

15. In a method as recited in claim 1, providing by way of said filter means a restricted path or cross-section small enough to prevent sperm from being carried along with fluid flowing through said path.

16. In a method as recited in claim 15, situating in the path of fluid flow in the vas a valve which in one position provides the restricted flow path and which in another position is fully open to provide substantially unrestricted flow so that in said other position of the valve sperm sufficient for conception can be carried along with the fluid.

17. In a method as recited in claim 15, situating in the path of fluid flow in the vas a valve which in one position provides substantially unrestricted flow of fluid and which in a second position places in the path of fluid flow said filter means which provides the restriction to the flow.

18. In a device for at least temporarily preventing conception, an implant small enough to be situated at least in part in a vas deferens and securing means for securing said implant at the vas deferens, said implant including a filter means for permitting vas fluid to flow through the vas deferens at all times, said filter means providing for the fluid, at least temporarily, a selective flow path across which said filter means extends and along which said filter means at least in part by filtration provides for the sperm a path along which said filter means acts, said filter means including means preventing in a mechanical, non-chemical manner viable sperm from being carried along with the fluid in numbers sufficient for conception.

19. The combination recited in claim 19, said filter means including a group of bodies adapted to be situated in a vas deferens and having a size, shape, and position relative to each other for forming a filter which retains sperm while permitting the fluid to flow past said bodies.

20. The conbination recited in claim 19 and wherein said bodies are made at least partly of a magnetic material.

21. The combination recited in claim 20 and wherein an enclosure means for extending at least partly across a vas deferens encloses the bodies and provides for said bodies a space in which the bodies can assume either a conception-preventing condition where they act as a filter or a conception-enabling condition where the bodies permit substantially unrestricted flow of fluid through the vas deferens.

22. In a device for at least temporarily preventing conception, implant means adapted to be connected with a vas deferens for permitting fluid to flow through the vas deferens at all times, said implant means providing for the fluid, at least temporarily, a selective flow and said implant means when providing said flow being adapted to act on fluid flowing through the vas to prevent viable sperm from being carried along with the fluid in numbers sufficient for conception, said implant means including a group of bodies adapted to be situated in a vas deferens and having a size, shape, and position relative to each other for forming a filter which retains sperm while permitting the fluid to flow without sperm past said bodies, said bodies being made at least partly of a magnetic material, and an enclosure means enclosing the bodies and providing for said bodies a space in which the bodies can assume either a conception-preventing condition where they act as a filter or a conception-enabling condition where the bodies permit substantially unrestricted flow of fluid through the vas deferens, and spring means cooperating with said bodies for urging them to assume the conception-enabling condition.

23. The combination of claim 22 and wherein said spring means includes elongated fine spring elements intermingled with said bodies.

24. The combination of claim 22 and wherein said spring means includes a springy compressible material surrounding at least some of said bodies.

25. In a device for at least temporarily preventing conception, implant means adapted to be connected with a vas deferens for permitting fluid to flow through the vas deferens at all times, said implant means providing for the fluid, at least temporarily, a selective flow and said implant means when providing said flow being adapted to act on fluid flowing through the vas to provide viable sperm from being carried along with the fluid in numbers sufficient for conception, said implant means including a group of bodies adapted to be situated in a vas deferens and having a size, shape, and position relative to each other for forming a filter which retains sperm while permitting the fluid to flow without sperm past said bodies, said bodies being made at least partly of a magnetic material, and an enclosure means enclosing the bodies and providing for said bodies a space in which the bodies can assume either a conception-preventing condition where they act as a filter or a conception-enabling condition where the bodies permit substantially unrestricted flow of fluid through the vas deferens, and inlet and outlet tubes respectively connected with opposed ends of said enclosure means for directing fluid into and out of the latter, said tubes carrying a tissue-ingrowth means and being adapted to be situated in the lumen of a vas deferens.

26. The combination of claim 25 and wherein one of said tubes extends through a substantial distance into the interior of said enclosure means defining therein around said one tube a space for accommodating said bodies when the latter are in their conception-enabling condition.

27. The combination of claim 25 and wherein said enclosure means extends laterally beyond said tubes to an extent sufficient for accommodating said bodies to one side of said tubes to provide said conception-enabling condition.

28. The combination of claim 19 and wherein said bodies are in the form of solid particles having sharp edges and points capable of injuring sperm to prevent the latter from flowing along with the fluid in the vas deferens in a condition where said sperm will be capable of achieving conception.

29. The combination of claim 19 and wherein a generating means is situated close enough to said enclosure means for generating a field for vibrating said bodies so that the vibrating bodies will act on the sperm to prevent the latter from having a condition where conception can take place.

30. The combination recited in claim 18 and comprising a valve means having two positions one of which is a partly open position providing said selective flow where said filter means acts at least in part by filtration and the other of which is a fully open position, said valve means in said partly open position restricting the flow of fluid through the vas to an extent sufficient to prevent sperm from being carried along with the fluid.

31. Implant means as recited in claim 18 and including a valve means having a pair of passages through which fluid can flow in a pair of different positions of said valve means, and one of said passages carrying said filter means, the latter providing a flow path restricted sufficiently to prevent sperm from being carried along with the fluid.

32. The combination recited in claim 18 and including a valve means having an inlet and an outlet and a housing between said inlet and outlet, said housing defining an interior space and a movable valve member situated in said interior space, said valve memeber having a substantially T-shaped bore for providing in one position a passage placing said inlet in communication with said outlet and in another position a passage providing communication between said inlet and a wall portion of said housing, said wall portion of said housing being formed with an opening communicating with said outlet and said opening carrying in its interior a filter means providing for fluid a path of flow restricted sufficiently to prevent sperm from being carried along with the fluid.

33. A variable filter comprising enclosure means small enough to be situated in the body of a living being and inlet and outlet means communicating with said enclosure means for directing fluid into and out of the latter, a plurality of magnetic bodies situated in said enclosure means in the path of the fluid flowing therethrough, and spring means in said enclosure means situated at least in part between said magnetic bodies and acting on said magnetic bodies for placing them in a condition providing substantially free flow of fluid through said enclosure means, while said bodies can be acted upon magnetically to attract each other with a force, in opposition to said spring means, sufficiently great to cause said bodies to assume a position with respect to each other which will restrict fluid flow to a predetermined degree.

34. The combination of claim 33 and wherein said spring means includes a plurality of elongated spring members intermingled with said bodies and urging them apart from each other.

35. The combination of claim 33 and wherein said spring means includes a plurality of resilient compressible layers respectively surrounding at least some of said bodies.

36. In a method for at least temporarily preventing the ejaculate of a male from containing viable sperm in numbers sufficient for conception, the step of at least temporarily providing for the flow of fluid through a vas deferens a selective flow which prevents viable sperm from being carried along with the fluid in numbers sufficient for conception, situating in the flow of fluid in a vas deferens a group of bodies which form a restricted path and permit fluid in the vas to flow past the bodies while acting on the sperm in the fluid to prevent the fluid which flows beyond the group of bodies from containing viable sperm in numbers sufficient for conception, the bodies being at least partly of a magnetic material, and including the steps of situating the bodies in an enclosure which is connected to the vas deferens for directing fluid therein through the interior of the enclosure and past the bodies situated therein, and acting on the magnetic properties of the bodies for placing them either in a conception-preventing condition where the bodies permit fluid to flow past the bodies while acting as a filter to prevent sperm from flowing past the bodies or in a conception-enabling condition where the bodies permit fluid in the vas with living sperm therein to flow freely past said bodies, and acting on the bodies with an alternating magnetic field to move the bodies with respect to each other and place them in a conception-enabling condition.

37. In a device for at least temporarily preventing conception, implant means adapted to be connected with a vas deferens for permitting fluid to flow through the vas deferens at all times, said implant means providing for the fluid, at least temporarily, a selective flow and said implant means when providing said flow being adapted to act on fluid flowing through the vas to prevent viable sperm from being carried along with the fluid in numbers sufficient for conception, said implant means including a group of bodies adapted to be situated in a vas deferens and having a size, shape, and position relative to each other for forming a filter which retains sperm while permitting the fluid to flow without sperm past said bodies, said bodies being in the form of solid particles having sharp edges and points capable of injuring sperm to prevent the latter from flowing along with the fluid in the vas deferens in a condition where said sperm will be capable of achieving conception, said bodies being diamond particles.

38. A variable flow device comprising an enclosure of a size to be situated in a body fluid passage of a living being and an inlet and outlet leading respectively to and from the enclosure, means for connecting said inlet and outlet to a tube in the body of a living being for directing fluid which flows through the tube through said inlet into said enclosure and then through said outlet out of said enclosure, and means in said enclosure for providing a selective flow of fluid therethrough, said means in said enclosure being made up at least in part of magnetic bodies between which fluid flows and which attract each other with a preselected force to provide a selective resistance to flow of fluid through the enclosure from the inlet to the outlet.

* * * * *

UNITED STATES PATENT AND TRADEMARK OFFICE
CERTIFICATE OF CORRECTION

PATENT NO. : 3,991,743
DATED : November 16, 1976
INVENTOR(S) : Louis Bucalo

It is certified that error appears in the above-identified patent and that said Letters Patent are hereby corrected as shown below:

Column 16, line 30, "19" (second occurrence) should read --18--.

Signed and Sealed this

Tenth Day of May 1977

[SEAL]

Attest:

RUTH C. MASON
*Attesting Officer*

C. MARSHALL DANN
*Commissioner of Patents and Trademarks*